United States Patent
Lichtenstein et al.

(10) Patent No.: US 7,837,610 B2
(45) Date of Patent: Nov. 23, 2010

(54) SYSTEM FOR IMPROVING DIASTOLIC DYSFUNCTION

(75) Inventors: Samuel Victor Lichtenstein, Vancouver (CA); Daniel Gelbart, Vancouver (CA); William Gelbart, Vancouver (CA)

(73) Assignee: Kardium Inc., Vancouver (CA)

( * ) Notice: Subject to any disclaimer, the term of this patent is extended or adjusted under 35 U.S.C. 154(b) by 501 days.

(21) Appl. No.: 11/497,309

(22) Filed: Aug. 2, 2006

(65) Prior Publication Data

US 2008/0045778 A1    Feb. 21, 2008

(51) Int. Cl.
*A61N 1/00* (2006.01)
(52) U.S. Cl. ............................................... 600/16
(58) Field of Classification Search ............ 600/16, 600/481, 508
See application file for complete search history.

(56) References Cited

U.S. PATENT DOCUMENTS

| | | | |
|---|---|---|---|
| 4,041,955 A | 8/1977 | Kelly et al. | |
| 4,114,202 A | 9/1978 | Roy et al. | 3/1.5 |
| 4,164,046 A | 8/1979 | Cooley | |
| 4,240,441 A | 12/1980 | Khalil | 128/692 |
| 4,263,680 A | 4/1981 | Reul et al. | 3/1.5 |
| 4,490,859 A | 1/1985 | Black et al. | 3/1.5 |
| 4,543,090 A | 9/1985 | McCoy | 604/95 |
| 4,794,912 A | 1/1989 | Lia | 128/4 |
| 4,850,957 A | 7/1989 | Summers | 604/22 |
| 4,890,602 A | 1/1990 | Hake | 128/4 |
| 4,890,612 A | 1/1990 | Kensey | 606/213 |
| 4,893,613 A | 1/1990 | Hake | 128/4 |
| 4,921,499 A | 5/1990 | Hoffman et al. | 623/16 |
| 5,021,059 A | 6/1991 | Kensey et al. | 606/213 |
| 5,047,047 A | 9/1991 | Yoon | 606/216 |
| 5,100,418 A | 3/1992 | Yoon et al. | 606/139 |
| 5,104,399 A | 4/1992 | Lazarus | 623/1 |
| 5,122,137 A | 6/1992 | Lennox | 606/40 |
| 5,192,314 A | 3/1993 | Daskalakis | 623/3 |
| 5,258,000 A | 11/1993 | Gianturco | 606/151 |
| 5,312,435 A | 5/1994 | Nash et al. | 606/213 |

(Continued)

FOREIGN PATENT DOCUMENTS

EP    2082690 A1    7/2009

(Continued)

OTHER PUBLICATIONS

Sharkey et al., "Left Ventricular Apex Occluder. Description of a Ventricular Partitioning Device," *Euro Intervention* 2:125-127, 2006.

(Continued)

*Primary Examiner*—George Manuel
*Assistant Examiner*—Shubatra Narayanaswamy
(74) *Attorney, Agent, or Firm*—Seed IP Law Group PLLC

(57) ABSTRACT

An elastic structure is introduced percutaneously into the left ventricle and attached to the walls of the ventricle. Over time the structure bonds firmly to the walls via scar tissue formation. The structure helps the ventricle expand and fill with blood during the diastolic period while having little affect on systolic performance. The structure also strengthens the ventricular walls and limits the effects of congestive heart failure, as the maximum expansion of the support structure is limited by flexible or elastic members.

20 Claims, 5 Drawing Sheets

U.S. PATENT DOCUMENTS

| | | | |
|---|---|---|---|
| 5,312,439 A | 5/1994 | Loeb | |
| 5,320,632 A | 6/1994 | Heidmueller | 606/144 |
| 5,364,408 A | 11/1994 | Gordon | 606/144 |
| 5,366,443 A | 11/1994 | Eggers et al. | 604/114 |
| 5,366,459 A | 11/1994 | Yoon | 606/151 |
| 5,368,601 A | 11/1994 | Sauer et al. | 606/144 |
| 5,450,860 A | 9/1995 | O'Connor | 128/898 |
| 5,478,353 A | 12/1995 | Yoon | 606/213 |
| 5,531,760 A | 7/1996 | Alwafaie | 606/216 |
| 5,593,424 A | 1/1997 | Northrup III | 606/232 |
| 5,713,896 A | 2/1998 | Nardella | 606/50 |
| 5,716,397 A | 2/1998 | Myers | 623/2 |
| 5,720,726 A | 2/1998 | Marcadis et al. | 604/96 |
| 5,728,114 A | 3/1998 | Evans et al. | 606/148 |
| 5,782,861 A | 7/1998 | Cragg et al. | 606/216 |
| 5,800,495 A | 9/1998 | Machek et al. | 607/116 |
| 5,824,066 A | 10/1998 | Gross | 623/2 |
| 5,836,990 A | 11/1998 | Li | 607/28 |
| 5,865,791 A | 2/1999 | Whayne et al. | 604/49 |
| 5,871,505 A | 2/1999 | Adams et al. | |
| 5,919,207 A | 7/1999 | Taheri | 606/219 |
| 5,961,440 A | 10/1999 | Schweich et al. | |
| 5,964,782 A | 10/1999 | Lafontaine et al. | 606/213 |
| 5,984,950 A | 11/1999 | Cragg et al. | 606/216 |
| 6,001,069 A | 12/1999 | Tachibana et al. | 601/2 |
| 6,024,096 A | 2/2000 | Buckberg | 128/898 |
| 6,104,944 A | 8/2000 | Martinelli | 600/424 |
| 6,113,610 A | 9/2000 | Poncet | 606/139 |
| 6,132,438 A | 10/2000 | Fleischman et al. | 606/139 |
| 6,203,554 B1 | 3/2001 | Roberts | 606/144 |
| 6,210,432 B1 | 4/2001 | Solem et al. | 623/1.15 |
| 6,214,032 B1 | 4/2001 | Loeb et al. | |
| 6,221,103 B1 | 4/2001 | Melvin | 623/3.1 |
| 6,221,104 B1 | 4/2001 | Buckberg et al. | 623/3.1 |
| 6,241,747 B1 | 6/2001 | Ruff | 606/216 |
| 6,248,124 B1 | 6/2001 | Pedros et al. | 606/213 |
| 6,258,258 B1 | 7/2001 | Sartori et al. | 208/263 |
| 6,287,321 B1 | 9/2001 | Jang | 606/200 |
| 6,304,769 B1 | 10/2001 | Arenson et al. | 600/424 |
| 6,306,135 B1 | 10/2001 | Ellman et al. | 606/45 |
| 6,332,864 B1 | 12/2001 | Schweich, Jr. et al. | 600/16 |
| 6,346,105 B1 | 2/2002 | Tu et al. | 606/41 |
| 6,358,258 B1 | 3/2002 | Arcia et al. | 606/139 |
| 6,360,749 B1 | 3/2002 | Jayaraman | 128/898 |
| 6,379,366 B1 | 4/2002 | Fleischman et al. | 606/139 |
| 6,391,048 B1 | 5/2002 | Ginn et al. | 606/213 |
| 6,391,054 B2 | 5/2002 | Carpentier et al. | 623/2.37 |
| 6,402,680 B2 | 6/2002 | Mortier et al. | 600/16 |
| 6,402,781 B1 | 6/2002 | Langberg et al. | 623/2.36 |
| 6,406,420 B1 | 6/2002 | McCarthy et al. | 600/16 |
| 6,409,760 B1 | 6/2002 | Melvin | 623/3.1 |
| 6,416,459 B1 | 7/2002 | Haindl | 600/37 |
| 6,436,052 B1 | 8/2002 | Nikolic et al. | 600/529 |
| 6,450,171 B1 | 9/2002 | Buckberg et al. | 128/898 |
| 6,475,223 B1 | 11/2002 | Werp et al. | 606/108 |
| 6,485,489 B2 | 11/2002 | Teirstein et al. | 606/41 |
| 6,506,210 B1 | 1/2003 | Kanner | 606/213 |
| 6,537,198 B1 | 3/2003 | Vidlund et al. | |
| 6,537,314 B2 | 3/2003 | Langberg et al. | 623/2.36 |
| 6,540,670 B1 | 4/2003 | Hirata et al. | 600/152 |
| 6,551,312 B2 | 4/2003 | Zhang et al. | 606/41 |
| 6,569,160 B1 | 5/2003 | Goldin et al. | 606/41 |
| 6,569,198 B1 | 5/2003 | Wilson et al. | 623/2.37 |
| 6,575,971 B2 | 6/2003 | Hauck et al. | 606/52 |
| 6,589,208 B2 | 7/2003 | Ewers et al. | 604/104 |
| 6,626,930 B1 | 9/2003 | Allen et al. | 606/213 |
| 6,632,238 B2 | 10/2003 | Ginn et al. | 606/213 |
| 6,662,034 B2 | 12/2003 | Segner et al. | 600/373 |
| 6,723,038 B1 | 4/2004 | Schroeder et al. | |
| 6,726,704 B1 | 4/2004 | Loshakove et al. | 606/213 |
| 6,726,716 B2 | 4/2004 | Marquez | 623/2.36 |
| 6,743,241 B2 | 6/2004 | Kerr | 606/144 |
| 6,749,622 B2 | 6/2004 | McGuckin, Jr. et al. | 606/213 |
| 6,760,616 B2 | 7/2004 | Hoey et al. | 600/547 |
| 6,780,197 B2 | 8/2004 | Roe et al. | 606/213 |
| 6,797,001 B2 | 9/2004 | Mathis et al. | 623/2.37 |
| 6,800,090 B2 | 10/2004 | Alferness et al. | 623/2.36 |
| 6,852,076 B2 | 2/2005 | Nikolic et al. | 600/37 |
| 6,855,143 B2 | 2/2005 | Davison et al. | 606/41 |
| 6,890,353 B2 | 5/2005 | Cohn et al. | 623/2.37 |
| 6,899,674 B2 | 5/2005 | Viebach et al. | 600/152 |
| 6,908,478 B2 | 6/2005 | Alferness et al. | 623/1.11 |
| 6,949,122 B2 | 9/2005 | Adams et al. | 623/2.36 |
| 6,960,229 B2 | 11/2005 | Mathis et al. | 623/2.36 |
| 6,986,775 B2 | 1/2006 | Morales et al. | 606/139 |
| 6,989,028 B2 | 1/2006 | Lashinski et al. | 623/2.37 |
| 6,994,093 B2 | 2/2006 | Murphy | |
| 6,997,951 B2 | 2/2006 | Solem et al. | 623/2.37 |
| 7,025,776 B1 | 4/2006 | Houser et al. | 606/213 |
| 7,050,848 B2 | 5/2006 | Hoey et al. | 600/547 |
| 7,052,487 B2 | 5/2006 | Cohn et al. | 604/509 |
| 7,144,363 B2 | 12/2006 | Pai et al. | 600/16 |
| 7,177,677 B2 | 2/2007 | Kaula et al. | 600/546 |
| 7,186,210 B2 | 3/2007 | Feld et al. | 600/16 |
| 7,189,202 B2 | 3/2007 | Lau et al. | 600/37 |
| 7,279,007 B2 | 10/2007 | Nikolic et al. | 623/11.11 |
| 7,300,435 B2 | 11/2007 | Wham et al. | 606/34 |
| 7,303,526 B2 | 12/2007 | Sharkey et al. | 600/37 |
| 7,507,252 B2 | 3/2009 | Lashinski et al. | 623/2.37 |
| 7,513,867 B2 | 4/2009 | Lichtenstein | |
| 2001/0003158 A1 | 6/2001 | Kensey et al. | 606/213 |
| 2001/0005787 A1 | 6/2001 | Oz et al. | 606/142 |
| 2001/0018611 A1 | 8/2001 | Solem et al. | 623/2.37 |
| 2001/0020126 A1 | 9/2001 | Swanson et al. | 600/407 |
| 2001/0044568 A1 | 11/2001 | Langberg et al. | 600/37 |
| 2002/0016628 A1 | 2/2002 | Langberg et al. | 623/2.36 |
| 2002/0026092 A1 | 2/2002 | Buckberg et al. | 600/37 |
| 2002/0055775 A1 | 5/2002 | Carpentier et al. | 623/2.17 |
| 2002/0087173 A1 | 7/2002 | Alferness et al. | 606/151 |
| 2002/0115944 A1 | 8/2002 | Mendes et al. | 600/594 |
| 2002/0161394 A1 | 10/2002 | Macoviak et al. | 606/200 |
| 2002/0161406 A1 | 10/2002 | Silvian | |
| 2002/0169359 A1 | 11/2002 | McCarthy et al. | 600/16 |
| 2002/0169360 A1 | 11/2002 | Taylor et al. | 600/37 |
| 2002/0169504 A1 | 11/2002 | Alferness et al. | 623/2.36 |
| 2002/0183836 A1 | 12/2002 | Liddicoat et al. | 623/2.11 |
| 2002/0183841 A1 | 12/2002 | Cohn et al. | 623/2.36 |
| 2002/0188170 A1 | 12/2002 | Santamore et al. | |
| 2002/0198603 A1 | 12/2002 | Buckberg et al. | 623/23.71 |
| 2003/0045896 A1* | 3/2003 | Murphy et al. | 606/191 |
| 2003/0050682 A1 | 3/2003 | Sharkey et al. | 607/126 |
| 2003/0050685 A1 | 3/2003 | Nikolic et al. | 623/1.11 |
| 2003/0069570 A1 | 4/2003 | Witzel et al. | 606/28 |
| 2003/0069636 A1 | 4/2003 | Solem et al. | 623/2.37 |
| 2003/0078465 A1 | 4/2003 | Pai et al. | |
| 2003/0078671 A1 | 4/2003 | Lesniak et al. | |
| 2003/0105384 A1 | 6/2003 | Sharkey et al. | 600/16 |
| 2003/0105520 A1 | 6/2003 | Alferness et al. | 623/2.36 |
| 2003/0109770 A1 | 6/2003 | Sharkey et al. | 600/16 |
| 2003/0149333 A1 | 8/2003 | Alferness | 600/16 |
| 2003/0163191 A1 | 8/2003 | Nikolic et al. | 623/1.11 |
| 2003/0220667 A1 | 11/2003 | van der Burg et al. | 606/200 |
| 2003/0229395 A1 | 12/2003 | Cox | 623/2.36 |
| 2004/0002626 A1 | 1/2004 | Feld et al. | 600/37 |
| 2004/0054279 A1 | 3/2004 | Hanley | 600/424 |
| 2004/0133273 A1 | 7/2004 | Cox | 623/2.11 |
| 2004/0138744 A1 | 7/2004 | Lashinski et al. | 623/2.36 |
| 2004/0153146 A1 | 8/2004 | Lashinski et al. | 623/2.36 |
| 2004/0158321 A1 | 8/2004 | Reuter et al. | 623/2.36 |
| 2004/0186566 A1 | 9/2004 | Hindrichs et al. | 623/2.37 |
| 2004/0215232 A1 | 10/2004 | Belhe et al. | 606/213 |
| 2004/0243170 A1 | 12/2004 | Suresh et al. | |
| 2004/0249408 A1 | 12/2004 | Murphy et al. | |
| 2004/0249453 A1 | 12/2004 | Cartledge et al. | 623/2.37 |

| | | | |
|---|---|---|---|
| 2004/0267358 A1 | 12/2004 | Reitan | 623/2.37 |
| 2005/0004668 A1 | 1/2005 | Aklog et al. | 623/2.36 |
| 2005/0015109 A1 | 1/2005 | Lichtenstein | |
| 2005/0054938 A1 | 3/2005 | Wehman et al. | 600/483 |
| 2005/0055089 A1 | 3/2005 | Macoviak et al. | 623/2.37 |
| 2005/0060030 A1 | 3/2005 | Lashinski et al. | 623/2.37 |
| 2005/0064665 A1 | 3/2005 | Han | 438/286 |
| 2005/0080402 A1 | 4/2005 | Santamore et al. | |
| 2005/0096047 A1 | 5/2005 | Haberman et al. | 455/432.3 |
| 2005/0107723 A1 | 5/2005 | Wehman et al. | 600/595 |
| 2005/0107871 A1 | 5/2005 | Realyvasquez et al. | 623/2.11 |
| 2005/0125030 A1 | 6/2005 | Forsberg et al. | 606/213 |
| 2005/0137700 A1 | 6/2005 | Spence et al. | 623/2.36 |
| 2005/0149014 A1 | 7/2005 | Hauck et al. | 606/41 |
| 2005/0149114 A1 | 7/2005 | Cartledge et al. | 606/213 |
| 2005/0154252 A1 | 7/2005 | Sharkey et al. | 600/37 |
| 2005/0182365 A1 | 8/2005 | Hennemann et al. | 604/113 |
| 2005/0187620 A1 | 8/2005 | Pai et al. | |
| 2005/0197692 A1 | 9/2005 | Pai et al. | |
| 2005/0197693 A1 | 9/2005 | Pai et al. | |
| 2005/0197694 A1 | 9/2005 | Pai et al. | |
| 2005/0197716 A1 | 9/2005 | Sharkey et al. | 623/23.67 |
| 2005/0209636 A1 | 9/2005 | Widomski et al. | 606/213 |
| 2005/0216052 A1 | 9/2005 | Mazzocchi et al. | 606/200 |
| 2005/0216054 A1 | 9/2005 | Widomski et al. | 606/213 |
| 2005/0240249 A1 | 10/2005 | Tu et al. | 607/96 |
| 2005/0251116 A1 | 11/2005 | Steinke et al. | 606/8 |
| 2005/0267574 A1 | 12/2005 | Cohn et al. | 623/2.36 |
| 2006/0004424 A1 | 1/2006 | Loeb et al. | |
| 2006/0014998 A1 | 1/2006 | Sharkey et al. | 600/16 |
| 2006/0015002 A1 | 1/2006 | Moaddeb et al. | |
| 2006/0015003 A1 | 1/2006 | Moaddes et al. | 600/37 |
| 2006/0015038 A1 | 1/2006 | Weymarn-Scharli | 600/585 |
| 2006/0025800 A1 | 2/2006 | Suresh | |
| 2006/0030881 A1 | 2/2006 | Sharkey et al. | 606/213 |
| 2006/0135968 A1 | 6/2006 | Schaller | |
| 2006/0135970 A1 | 6/2006 | Schaller | |
| 2006/0184242 A1 | 8/2006 | Lichtenstein | 623/2.37 |
| 2006/0199995 A1 | 9/2006 | Vijay | 600/37 |
| 2006/0229491 A1 | 10/2006 | Sharkey et al. | 600/37 |
| 2006/0235286 A1 | 10/2006 | Stone et al. | 600/381 |
| 2006/0241334 A1 | 10/2006 | Dubi et al. | 600/16 |
| 2006/0264980 A1 | 11/2006 | Khairkhahan et al. | 606/153 |
| 2006/0276683 A1 | 12/2006 | Feld et al. | 600/16 |
| 2006/0281965 A1 | 12/2006 | Khairkhahan et al. | 600/37 |
| 2006/0293698 A1 | 12/2006 | Douk | 606/142 |
| 2007/0016068 A1 | 1/2007 | Grunwald et al. | 600/468 |
| 2007/0118215 A1 | 5/2007 | Moaddeb | 623/2.37 |
| 2007/0161846 A1 | 7/2007 | Nikolic et al. | 600/16 |
| 2007/0198058 A1 | 8/2007 | Gelbart et al. | 606/213 |
| 2007/0213578 A1 | 9/2007 | Khairkhahan et al. | 600/16 |
| 2007/0213815 A1 | 9/2007 | Khairkhahan et al. | 623/3.1 |
| 2007/0250160 A1 | 10/2007 | Rafiee | 623/2.11 |
| 2007/0270688 A1 | 11/2007 | Gelbart et al. | 600/427 |
| 2008/0004643 A1 | 1/2008 | To et al. | 606/159 |
| 2008/0004697 A1 | 1/2008 | Lichtenstein et al. | 623/2.11 |
| 2008/0045778 A1 | 2/2008 | Lichtenstein et al. | 600/16 |
| 2008/0071298 A1 | 3/2008 | Khairkhahan et al. | 606/151 |
| 2008/0086164 A1 | 4/2008 | Rowe | 606/191 |
| 2009/0192539 A1 | 7/2009 | Lichtenstein | |

FOREIGN PATENT DOCUMENTS

| | | |
|---|---|---|
| WO | 90/15582 | 12/1990 |
| WO | 01/78625 | 10/2001 |
| WO | 03/015611 | 2/2003 |
| WO | 03/077800 | 9/2003 |
| WO | 2004012629 | 2/2004 |
| WO | 2004047679 | 6/2004 |
| WO | 2004/084746 | 10/2004 |
| WO | 2004100803 | 11/2004 |
| WO | 2005/046520 | 5/2005 |
| WO | 2005070330 | 8/2005 |
| WO | 2005102181 | 11/2005 |
| WO | 2006017809 | 2/2006 |
| WO | 2006135747 | 12/2006 |
| WO | 2006135749 | 12/2006 |
| WO | 2007021647 | 2/2007 |
| WO | 2007/115390 | 10/2007 |

OTHER PUBLICATIONS

Otasevic et al., "First-in-Man Implantation of Left Ventricular Partitioning Device in a Patient With Chronic Heart Failure: Twelve-Month Follow-up," *Journal of Cardiac Failure* 13(7):517-520, 2007.

U.S. Appl. No. 10/690,131, filed Oct. 20, 2003, Lichtenstein.

U.S. Appl. No. 12/120,195, filed May 13, 2008, Dahlgren et al.

Athanasuleas et al., "Surgical Anterior Ventricular Restoration for Ischemic Cardiomyopathy," *Operative Techniques in Thoracic and Cardiovascular Surgery* 7(2):66-75, May 2002.

Buchbinder, MD, "Dynamic Mitral Valve Annuloplasty: A Reshapable Ring for Residual and Recurring MR," from the *Foundation for Cardiovascular Medicine*, La Jolla, CA. May 24, 2007.

CardioSeal Product Brochure, URL=http://nmtmedical.com/products/ci/index.htm, download date: May 13, 2006.

Cooley, "Ventricular Aneurysms and Akinesis," *Cleveland Clinic Quarterly* 45(1):130-132, 1978.

David et al., "Postinfarction Ventricular Septal Rupture: Repair by Endocardial Patch with Infarct Exclusion," *Journal of Thoracic and Cardiovascular Surgery* 110(5):1315-1322, 1995.

Dor et al., "Left Ventricular Aneurysm: A New Surgical Approach," *Thoracic Cardiovascular Surgery* 37:11-19, 1989.

Dor et al., "Late Hemodynamic Results After Left Ventricular Patch Repair Associated with Coronary Grafting in Patients with Postinfarction Akinetic or Dyskinetic Aneurysm of the Left Ventricle," *Journal of Thoracic and Cardiovascular Surgery* 110(5):1291-1301, 1995.

Dor, "Left Ventricular Aneurysms: The Endoventricular Circular Patch Plasty," *Seminars in Thoracic and Cardiovascular Surgery* 9(2):123-130, Apr. 1997.

Jatene, "Left Ventricular Aneurysmectomy," *Journal of Thoracic and Cardiovascular Surgery* 89(3):321-331, 1985.

Konings et al., "Development of an Intravascular Impedance Catheter for Detection of Fatty Lesions in Arteries," *IEEE Transactions on Medical Imaging* 16(4):439-446, 1997.

Mack, "New Techniques for Percutaneous Repair of the Mitral Valve," *Heart Failure Review* 11:259-268, 2006.

Menicanti et al., "The Dor Procedure: What has Changed After Fifteen Years of Clinical Practice?" *Journal of Thoracic and Cardiovascular Surgery* 124(5):886-890, Nov. 2002.

Rivera et al., "Ventricular Aneurysms and Akinesis," *Cleveland Clinic Quarterly* 45(1):133-135, 1978.

Stiles et al., "Simulated Characterization of Atherosclerotic Lesions in the Coronary Arteries by Measurement of Bioimpedance," *IEEE Transactions on Biomedical Engineering* 50(7):916-921, 2003.

Tanaka et al., "Artificial SMA Valve for Treatment of Urinary Incontinence: Upgrading of Valve and Introduction of Transcutaneous Transformer," *Bio-Medical Materials and Engineering* 9:97-112, 1999.

Timek et al., "Septal-Lateral Annular Cinching ('SLAC') Reduces Mitral Annular Size Without Perturbing Normal Annular Dynamics," *Journal of Heart Valve Disease* 11(1):2-10, 2002.

Timek et al., "Septal-Lateral Annular Cinching Abolishes Acute Ischemic Mitral Regurgitation," *Journal of Thoracic and Cardiovascular Surgery* 123(5):881-888, 2002.

Torrent-Guasp et al., "Spatial Orientation of the Ventricular Muscle Band and Approach to Partial Ventriculotomy in Heart Failure," *Pathogenesis and Treatment*, Ch. 36, pp. 685-693.

Valvano et al., "Thermal Conductivity and Diffusivity of Biomaterials Measured with Self-Heated Thermistors," *International Journal of Thermodynamics* 6(3):301-311, 1985.

Extended European Search Report, mailed Jun. 26, 2008, for EP08100878.1, 11 pages.

Lichtenstein, "Methods and Devices for Altering Blood Flow Through the Left Ventricle," Preliminary Amendment mailed Mar. 6, 2006 for U.S. Appl. No. 10/571,165, 7 pages.

Lichtenstein, "Methods and Devices for Altering Blood Flow Through the Left Ventricle," Office Action mailed Mar. 26, 2007 for U.S. Appl. No. 10/622,129, 17 pages.

Lichtenstein, "Methods and Devices for Altering Blood Flow Through the Left Ventricle," Amendment mailed Jul. 26, 2007 for U.S. Appl. No. 10/622,129, 17 pages.

Lichtenstein, "Methods and Devices for Altering Blood Flow Through the Left Ventricle," Office Action mailed Nov. 14, 2007 for U.S. Appl. No. 10/622,129, 6 pages.

Lichtenstein, "Methods and Devices for Altering Blood Flow Through the Left Ventricle," Preliminary Amendment mailed Feb. 14, 2008 for U.S. Appl. No. 10/622,129, 15 pages.

Lichtenstein, "Methods and Devices for Altering Blood Flow Through the Left Ventricle," Examiner's Amendment mailed Mar. 2, 2009 for U.S. Appl. No. 10/622,129, 5 pages.

\* cited by examiner

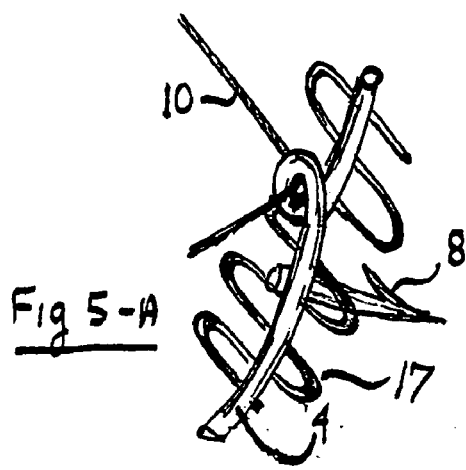
Fig 5-A
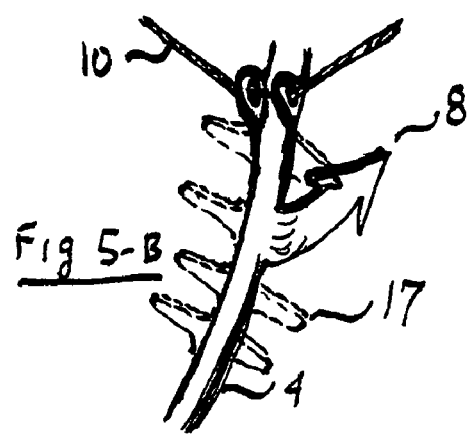
Fig 5-B
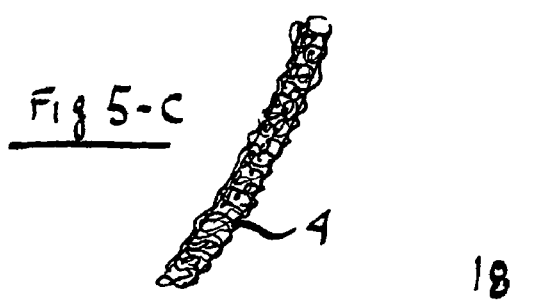
Fig 5-C
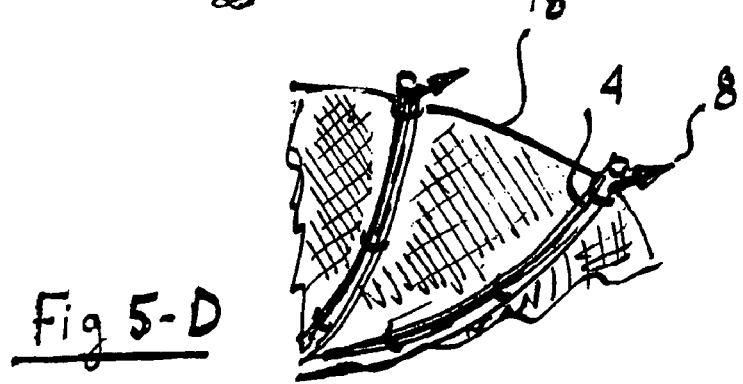
Fig 5-D

SYSTEM FOR IMPROVING DIASTOLIC DYSFUNCTION

FIELD OF THE INVENTION

This application relates to cardiac surgery, and in particular to methods of treating heart failure such as congestive heart failure and diastolic dysfunction by percutaneous surgery.

BACKGROUND OF THE INVENTION

Diastolic dysfunction (i.e., insufficient expansion of the left ventricle during the diastolic phase) and general deterioration of the left ventricular performance are very common problems, affecting about 5 million people in the US alone. The problems can be triggered by a myocardial infraction or develop slowly over time. More background data on congestive heart failure can be found on the internet at: http://healthlink.mcw.edu/article/928348606.html and many other medical sources.

Prior art treatment can be classified generally into three methods: surgery to change the shape of the left ventricle, wrapping the heart in an elastic net, or introducing a reinforcing structures via a catheter into the left ventricle. The first two methods require extensive surgery. The prior art minimally invasive or percutaneous procedures such as disclosed by US patent applications 2005/0015109; 2004/0243170; 2004/0249408 and 2006/0025800 addressed the need of strengthening the heart wall to resist remodeling and enlargement due to systolic pressure, but do not improve diastolic expansion to allow better filling of the left ventricle with blood. In many cases prior art methods actually sacrifice diastolic function in exchange for preventing the abnormal enlargement of the left ventricle that often follows myocardial infraction. For example, wrapping the heart in an elastic net will assist systolic action and will limit left ventricle enlargement, but will interfere with diastolic function as it will require more force to expand the left ventricle and stretch the net. The same is true for any rigid internal reinforcement.

SUMMARY OF THE INVENTION

As taught herein a system may assist diastolic function, the system being able to fit through a catheter and be installed percutaneously. The system may also limit the enlargement of the left ventricle, thus solving two major problem of congestive heart failure in a single percutaneous procedure. Further advantages will become clear by studying the disclosure and the drawings.

An elastic structure is introduced percutaneously into the left ventricle and attached to the walls of the ventricle. Over time the structure bonds firmly to the walls via scar tissue formation. The structure helps the ventricle expand and fill with blood during the diastolic period while having little affect on systolic performance. The structure also strengthens the ventricular walls and limits the effects of congestive heart failure, as the maximum expansion of the support structure is limited by flexible or elastic members.

BRIEF DESCRIPTION OF THE DRAWINGS

FIG. 2-B is a cross sectional view of the left ventricle of the heart after deployment of the device of FIG. 1 therein.

FIGS. 5-A, 5-B, 5-C and 5-D show different embodiments of the cardiac device, according to further illustrated embodiments.

DETAILED DESCRIPTION OF THE INVENTION

Various embodiments of a cardiac device comprise an elastic structure that it introduced into a left ventricle of a heart and assists diastolic function by gently trying to expand the left ventricle. The elastic force is a small fraction of the force during systolic contraction, thus the device has little effect on the systolic pressure or ejected volume. It is well known that diastolic dysfunction is a major cause of cardiovascular failure, as it is far more common than systolic dysfunction. After some time (weeks to months) scar tissue permanently binds the elastic structure of the device to the ventricular wall. At this point the device also prevents ventricular enlargement, acting as reinforcement to the ventricular wall and limiting the maximum size of the left ventricle. Since the enlargement of the left ventricle as a result of congestive heart failure or infarct is gradual, scar tissue will have a chance to form before full bond strength is required between the elastic structure of the device and the ventricular wall.

Figure 1:
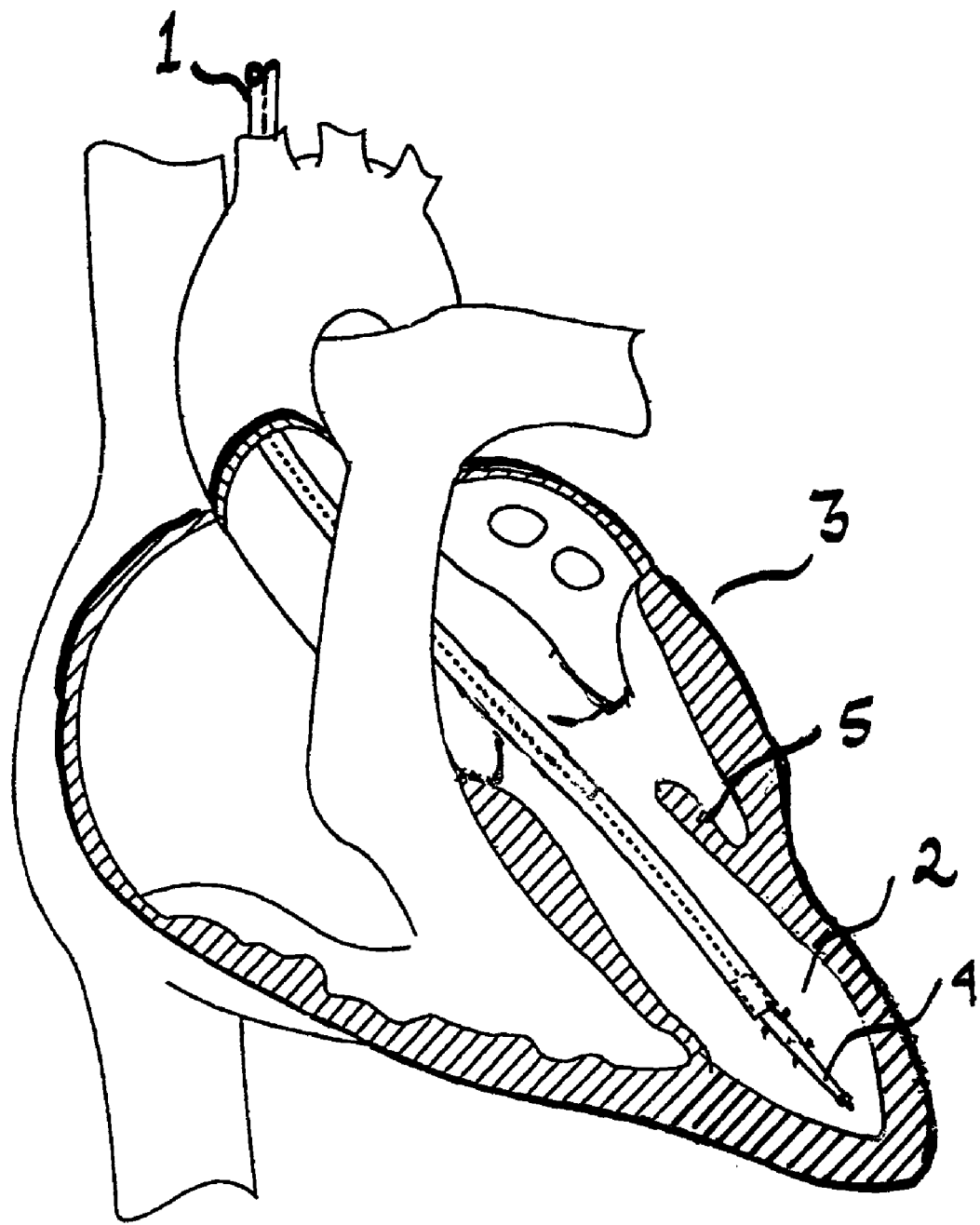
FIG. 1 is a cross sectional view of a heart showing an embodiment a cardiac device deployed in a left ventricle of the heart.

FIG. 1 shows a typical deployment of a cardiac device 4 according to one illustrated embodiment of the invention. Deployment is performed via a catheter 1 inserted through the aorta into a left ventricle 2 of a heart 3. Any method of accessing the left ventricle can be used, such as trans-septal or via the apex of the left ventricle. The catheter size is in the same range as other percutaneous cardiac procedures, using sizes in the range of 18 Fr to 28 Fr (about 6 to 9 mm). The cross section also shows the papillary muscles 5 and device 4.

Figure 2:
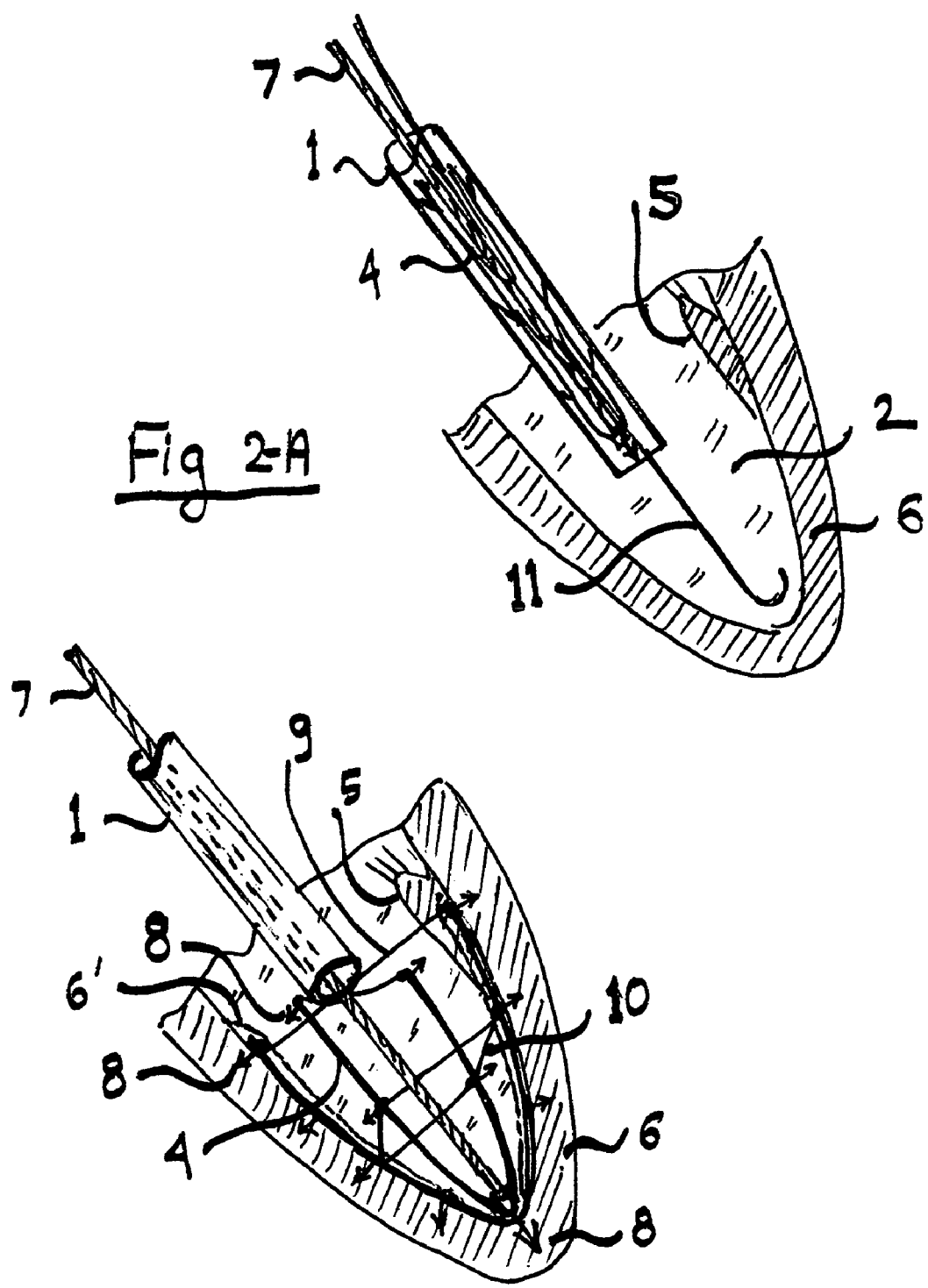
FIG. 2-A is a cross sectional view of the left ventricle of the heart with the device of FIG. 1 still in a catheter.

FIG. 2-A shows the device 4 still inside catheter 1. Device 4 is held by flexible cable 7 which is used to push the device 4 through the catheter 1, typically via a hemostatic seal outside the body (not shown). Typically a guide wire 11 is used to guide the catheter 1 into the left ventricle 2.

FIG. 2-B shows the device 4 after deployment in the left ventricle 2 of a heart 3. The device 4 expands elastically to fill the left ventricle 2. Ventricular contractions help embed a number of barbs 8 into a ventricular wall 6. Over time, scar tissue 6' forms a permanent bond between the device 4 and the ventricular wall 6. The maximum opening of the device 4 is limited not only by the ventricular wall 6 but by flexible cross-members 9 and 10. It is desired to connect members 9 across the device 4 rather than between adjacent arms (as shown by reference numeral 10) as this allows the cross member to clear the papillary muscles, allowing the device 4 to cover a larger part of the left ventricle 2. As seen in FIG. 2B, the papillary muscles 5 can fit between two elastic members of device 4.

Figure 3:
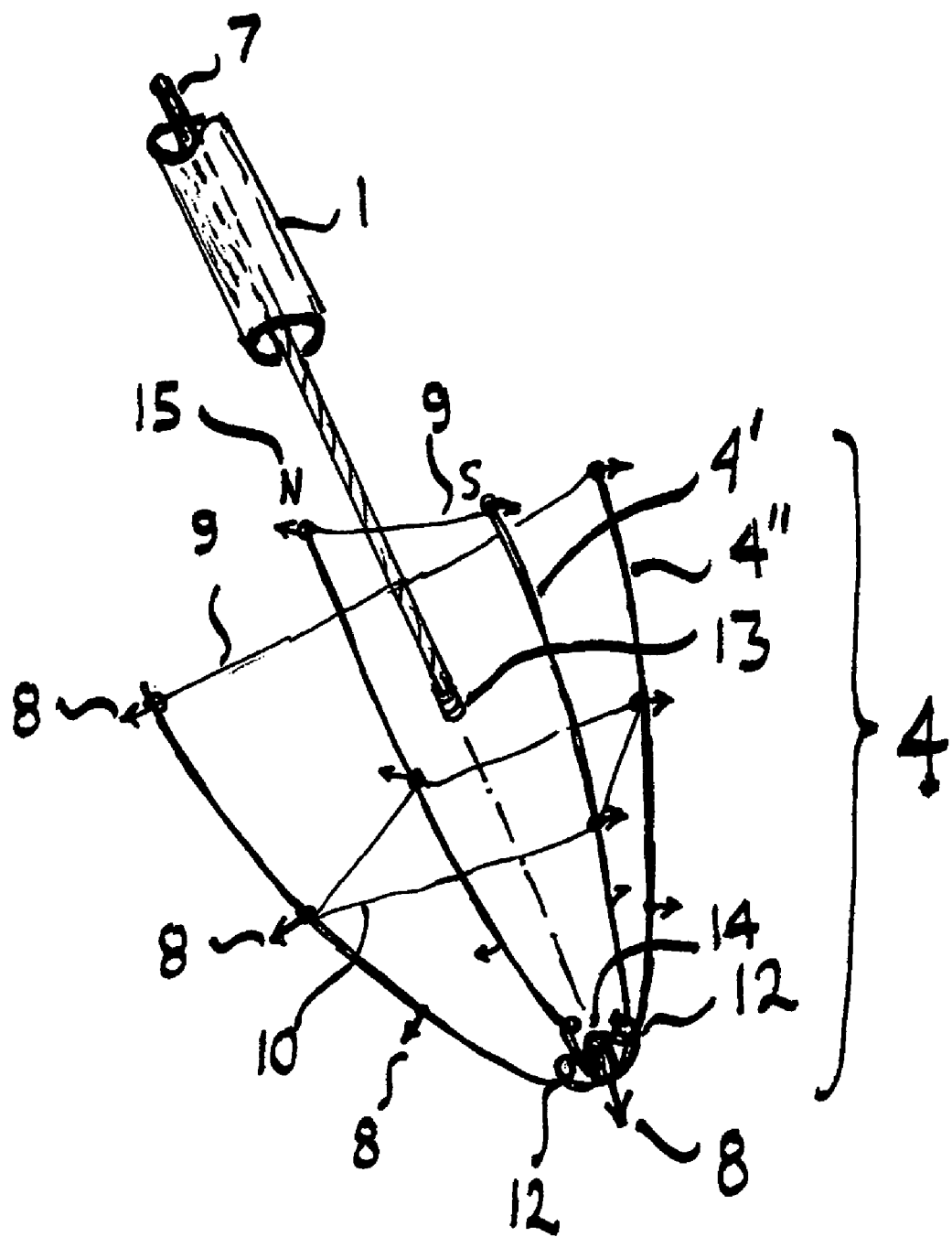
FIG. 3 is a perspective view of an embodiment of the invention.

FIG. 3 provides a more detailed view of the device of FIGS. 1, 2-A and 2-B. The cardiac device 4 has two pairs of elastic arms 4' and 4". The arms 4' and 4" are equipped with barbs 8 and cross members 9 and 10. The arms 4' and 4" can be made from any durable elastic material such Nitinol, spring tempered stainless steel, plated beryllium copper or polymeric material. For added elasticity small loops 12 can be added. At an apex of the device 4 a connector 14, such as a thread, is used for temporary attachment to the flexible cable 7 via a thread 13. Cross members 9 and 10 can be flexible steel cables, polymeric cables, flexible ribbons or similar flexible members. The purpose of members 9 and 10 is to limit the maximum dilation of the ventricle 2 and stop ventricular enlargement (after members 4' and 4" bond to ventricle wall 6 by scar tissue 6').

The number of flexible members 4' and 4" of device 4 and number of cross members 9, 10 can vary, the preferred embodiment having from three to twelve elastic members 9, 10. Cross members 9, 10 can connect adjacent elastic members 4' and 4" as members 10 do, or connect opposing members 4' and 4" as members 9 do. The arrangement shown in FIG. 3 is desired in order to allow elastic members 4' and 4" to extend beyond the papillary muscles 5 without cross members 9 touching the papillary muscles 5 or mitral valve cords (also known as chordae tendineae). Like any spring, the force that elastic members 4' and 4" exert on ventricle wall 6 is F=k(x+a), "k" being the spring constant, "a" the preload (amount of spring preload beyond the fully dilated position) and "x" the ventricular wall movement. The spring constant k is selected not to interfere with systolic function while still helping diastolic filling. By the way of example, a total force the ventricular wall 6 is capable of exerting on each one of the elastic members 4' and 4" is about 20-30 Nt (about 2-3 Kg) and the average movement during contraction is about 1-2 cm. In order to limit the effect on systolic operation the total force is chosen to be below 10% of systolic force, or about 2 Nt. If a preload of 2 cm is chosen, the spring constant can be calculated from the equation: 2 Nt=k(0.02 m+0.02 m), k=50 Nt/m. The size (i.e., diameter) of wire forming elastic members 4' and 4" is determined by the spring constant k. The size is typically in the range of 0.5-1 mm.

In order to place the device 4 correctly relative to the papillary muscles 5 the orientation of the device 4 inside the left ventricle 6 needs to be known. This can be done by fluoroscopy, ultrasound or by other location methods such as magnetizing elastic members 4' but not 4". This creates a north and south pole 15 which can be detected from outside the body by a magnetometer (or even a very sensitive magnetic compass).

Figure 4:
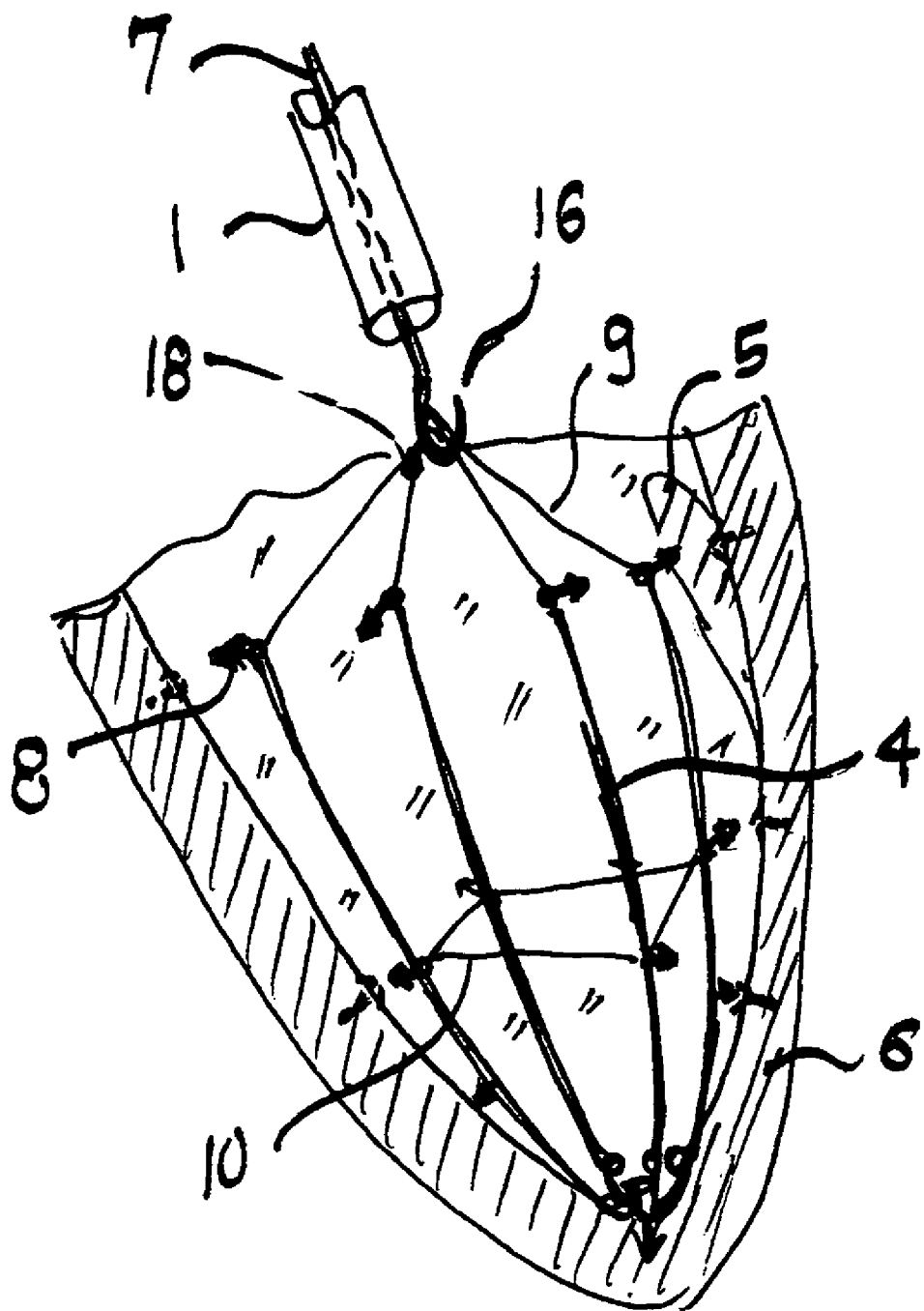
FIG. 4 is a cross sectional view of a left ventricle of a heart showing a device being retrieved therefrom using a catheter.

The design of the device 4 allows aborting the deployment at any stage and retrieving the device 4. This is illustrated in FIG. 4. A flexible cable 7 terminating in a hook 16 is introduced via a catheter 1.

Cross members 9 are snagged by the hook 16 and the device 4 is pulled back into the catheter 1. If retrieval is desirable the two cross members 9 should be permanently joined at a cross-over point 18. This allows the hook 16 to self-center regardless of the point at which the hook 16 snagged cross members 9 and regardless whether the hook 16 has snagged one or both cross members 9. Obviously the retrieval is much more difficult once scar tissue 6' has developed.

FIGS. 5-A through 5-D offer a more detailed close-up view of the construction of the device 4. FIG. 5-A shows the elastic elements 4' and 4" of the device 4 made of spring wire, cross members 10 made of thin stainless steel cable and barb 8 made of steel wire spot welded to the remainder of the device 4. If needed, a load spreading structure 17 can be added. The load spreading structure 17 can be made of bent wire, spot welded to remainder of the device 4 as shown, or can take the form of a polymeric strip. The complete device 4 can be coated with an anti-coagulant coating, drug eluting coating or any beneficial coating well known from the art of stents.

FIG. 5-B shows an alternate illustrated embodiment, cut out from a single sheet of elastic material and bent to shape. This mode of construction particularly advantageous when device 4 is made of Nitinol, as Nitinol is difficult to join. As before, an optional load spreading structure 17 can be added.

FIG. 5-C shows an embodiment of a device 4 that does not use discrete barbs but providing elastic members 4 with a special surface finish to promote rapid bonding with ventricular wall 6. Some examples of such finishes are: porous surfaces, surfaces coated with biological adhesives, surfaces coated with miniature barbs similar to the well known Velcro® fastener (generically termed hook and loop fastener), growth-promoting drug coating etc. It is known in the art that velour-like finishes promote tissue infiltration and greatly increase bonding strength. Test results are listed in U.S. Pat. No. 4,164,046 hereby incorporated by reference.

FIG. 5-D shows an embodiment in which the cross members are replaced with a continuous layer of a flexible mesh or flexible hemostatic material 18, such as Dacron fabric. When the layer 18 is hemostatic the device 4 can also seal an aneurysm or puncture in the ventricular wall 6, while still providing the other stated benefits. This is particularly desirable when the ventricular wall 6 is already significantly thinned by enlargement.

While the examples shown use a catheter 1 to enter the left ventricle 6 via the mitral valve, it is obvious that various other techniques may be employed to deploy the device 4. The device 4 can be installed in the left ventricle 6 also via the aortic valve, by piercing an apex of the left ventricle 6 or by an incision at any convenient point. It can be used percutaneously or during conventional cardiac surgery.

What is claimed is:

1. A method of treating diastolic dysfunction as well as ventricular enlargement, comprising:
    inserting a structure having a plurality of elastic arms physically coupled together proximate one end of the elastic arms and at least one flexible cross-member expansion limiter structure coupled to a respective pair of non-successively adjacent ones of the elastic arms across the structure to limit an expansion of the elastic arms into a left ventricle of a heart; and
    positioning the structure such that portions of the elastic arms of the structure when expanded contact respective portions of a wall that forms the left ventricle at locations spaced relatively above a point at which a set of papillary muscles extend from the wall which is spaced relatively above an apex of the left ventricle and a portion of the structure is spaced relatively below the point at which the set of papillary muscles extend from the wall that forms the left ventricle without either the elastic arms or the at least one flexible cross-member expansion limiter structure interfering with the papillary muscles or with a number of chordae tendineae that extend from the papillary muscles, wherein the elastic arms assist an expansion of the left ventricle during a diastolic phase of a cardiac cycle and the expansion limiter structure prevents a ventricular enlargement.

2. The method of claim 1, further comprising:
    causing portions of the elastic arms to attach to respective portions of the wall that forms the left ventricle at the locations spaced relatively above the point at which the set of papillary muscles extend from the wall.

3. The method of claim 1, further comprising:
    permanently bond the structure to ventricular walls by tissue formation having a bond strength sufficient to resist ventricular enlargement over time.

4. The method of claim 1 wherein inserting the structure includes delivering the structure via a catheter.

5. The method of claim 1, further comprising:
    retrieving the structure from the left ventricle via a catheter.

6. The method of claim 1 wherein inserting a structure includes inserting the structure having at least some parts of the structure made of a flexible metal wire.

7. The method of claim 1 wherein inserting a structure includes inserting a structure having at least some parts made of a polymeric material.

8. The method of claim 1 wherein inserting a structure includes inserting a structure which bears a biologically beneficial coating.

9. The method of claim 1, further comprising:
orienting the structure to clear the papillary muscles.

10. The method of claim 1 wherein the structure initially attaches itself to the walls of the left ventricle with sharp barbs.

11. The method of claim 1 wherein the structure initially attaches itself to the walls of the left ventricle by elastic pressure.

12. The method of claim 1 wherein inserting a structure includes inserting the structure having the expansion limiter structure spaced relatively inwardly from a distal end of the elastic arms.

13. A cardiac medical device, comprising:
a plurality of elastic arms physically coupled together, the elastic arms movable between a first configuration in which the medical device is sized to be inserted into a left ventricle of a heart and a second configuration in which the plurality of elastic arms physically engage portions of a wall that forms the left ventricle to assist an expansion of the left ventricle during a diastolic phase of a cardiac cycle; and
at least one flexible cross-member expansion limiter structure coupled to a respective pair of the elastic arms across the structure to limit an expansion of the elastic arms to prevent a ventricular enlargement, wherein the elastic arms of the pair of elastic arms that are coupled by the flexible cross-member are not successively adjacent to one another,
wherein the elastic arms are sized to contact respective portions of the wall at locations spaced relatively above a point at which a set of papillary muscles extend from the wall without either the elastic arms or the at least one expansion limiter structure interfering with the papillary muscles or with a number of chordae tendineae that extend from the papillary muscles and with a portion of the device positioned relatively below the point at which the set of papillary muscles extend from the wall.

14. The cardiac medical device of claim 13 wherein the plurality of elastic arms and the at least one flexible cross-member are configurable to be delivered a catheter.

15. The cardiac medical device of claim 13, further comprising:
a coupling structure that allows the cardiac medical device to be retrieving the structure from the left ventricle via a catheter.

16. The cardiac medical device of claim 13 wherein at least one of the plurality of elastic arms and the at least one flexible cross-member are made of a flexible metal wire.

17. The cardiac medical device of claim 13 wherein at least one of the plurality of elastic arms or the at least one flexible cross-member are made of a polymeric material.

18. The cardiac medical device of claim 13 wherein at least one of the plurality of elastic arms or the at least one flexible cross-member bear a biologically beneficial coating.

19. The cardiac medical device of claim 13 wherein at least one of the plurality of elastic arms includes a sharp barb receivable in the wall.

20. The cardiac medical device of claim 13 wherein the flexible cross-member expansion limiter structure is spaced relatively inwardly from a distal end of the elastic arms.

* * * * *